United States Patent
Sundberg et al.

(10) Patent No.: US 12,110,511 B2
(45) Date of Patent: Oct. 8, 2024

(54) METHODS AND CULTURE MEDIA FOR PRODUCTION, QUANTIFICATION AND ISOLATION OF BACTERIOPHAGES

(71) Applicant: Jyväskylän yliopisto, Jyväskylän yliopisto (FI)

(72) Inventors: Lotta-Riina Sundberg, Jyväskylä (FI); Gabriel Almeida, Jyväskylä (FI); Elina Laanto, Jyväskylä (FI)

(73) Assignee: Jyväskylän yliopisto, Jyväskylän yliopisto (FI)

( * ) Notice: Subject to any disclaimer, the term of this patent is extended or adjusted under 35 U.S.C. 154(b) by 1014 days.

(21) Appl. No.: 16/966,472

(22) PCT Filed: Jan. 31, 2019

(86) PCT No.: PCT/FI2019/050073
§ 371 (c)(1),
(2) Date: Jul. 31, 2020

(87) PCT Pub. No.: WO2019/150003
PCT Pub. Date: Aug. 8, 2019

(65) Prior Publication Data
US 2021/0047625 A1 Feb. 18, 2021

(30) Foreign Application Priority Data
Jan. 31, 2018 (FI) .................................... 20185086

(51) Int. Cl.
*C12N 7/00* (2006.01)
(52) U.S. Cl.
CPC ...... *C12N 7/00* (2013.01); *C12N 2795/00021* (2013.01); *C12N 2795/00051* (2013.01)
(58) Field of Classification Search
CPC ............ C12N 7/00; C12N 2795/00021; C12N 2795/00051
See application file for complete search history.

(56) References Cited

FOREIGN PATENT DOCUMENTS

| CN | 104651266 A | 5/2015 |
|---|---|---|
| WO | WO2014055127 A1 | 4/2014 |
| WO | WO2016081645 A1 | 5/2016 |

OTHER PUBLICATIONS

Barr et al: Bacteriophage adhering to mucus provide a non-host-derived immunity. Proceedings of the National Academmy of Sciences, 2013, vol. 110, pp. 10771-10776.
Bradbury: Mucosal infection yields to new approaches. LANCET, 2000, vol. 356(9238), p. 1332.
Holmgren et al: Mucosal immunity and vaccines. Nat Med, 2005, vol. 11 (4S), p. S45.
Iwase et al: Release of oligosaccharides possesing reducing-end N-acetylgalactosamine from mucus glycoprotein in *Streptomyces* sp. OH-11242 culture medium through action of endo-type glycosidase. Biochemical and Biophysical Research Communications, Feb. 1988, vol. 151, No. 1, pp. 422-428.
Janda et al: The genus *Aeromonas*: Taxonomy, pathogenicity, and infection. Clin Microbiol Rev, 2010.
Klesius et al: Chemotactic factors of Flavobacterium columnare to skin mucus of healthy channel catfish (*Ictalurus punctatus*). FEMS Microbiology Letters, 2010, vol. 310, pp. 145-151.
Klesius et al: Flavobacterium columnare chemotaxis to channel catfish mucus. FEMS Microbiology Letters, 2008, vol. 288, pp. 216-220.
Laanto et al: Phage specificity of the freshwater fish pathogen *Flavobacterium columnare*. Applied and Environmental Microbiology, 2011, vol. 77, pp. 7868-7872.
Laanto et al: Phage-driven loss of virulence in a fish pathogenic bacterium. Plos One, Dec. 2012, vol. 7, No. 12, pp. 1-8.
Laanto et al: The use of phage FCL-2 as an alternative to chemotherapy against columnaris disease in aquaculture. Frontiers in Microbiology, 2016, vol. 6.
Miura et al: Purification and characterization of extracellular 1,2-alpha-L-fucosidase from Bacillus cereus. Journal of Bioscience and Bioengineering, 2005, vol. 99, No. 6, pp. 629-635.
Joo et al: Proteomic Analysis of Pure Human Airway Gland Mucus Reveals a Large Component of Protective Proteins. Plos One, 2015.02.23, vol. 10, No. 2.
Shoemaker et al: Growth and survival of the fish pathogenic bacterium, Flavobacterium columnare, in tilapia mucus and porcine gastric mucin. Fems Microbiology Letters, Feb. 2015, vol. 362, No. 4, pp. 1-5.
Song et al: Comparison of Six Media for the Cultivation of Flexibacter columnaris. Fish Pathology, 1988, vol. 23, pp. 91-94.
Staroscik et al: The influence of salmon surface mucus on the growth of Flavobacterium columnare. Journal of Fish Diseases, Jan. 2008, vol. 31, No. 1, pp. 59-69.
Wikipedia: Lysogeny broth data sheet. https://en.wikipedia.org/w/index.php?title=Lysogeny_broth&oldid=913830038.

*Primary Examiner* — Janet L Andres
*Assistant Examiner* — Ruixue Wang
(74) *Attorney, Agent, or Firm* — Laine IP Oy (57) ABSTRACT

The present invention is directed to a method for producing bacteriophages infecting a bacterial host such as *Flavobacterium columnare* or *Aeromonas* sp, the method comprising the steps of adding the bacterium to a sterile culture medium supplemented with mucin or another mucus component, incubating said culture medium, thereby obtaining a bacterial culture, optionally collecting the supernatant containing floating (planktonic) bacterial cells from said culture and transferring the supernatant to a new container in order to discard most of the biofilm and adding a bacteriophage infecting the bacterium to said bacterial culture obtained from a previous step, and incubating the culture until the phage yield increases or peaks. The method can also be used for preparing modified enrichment cultures for optimized phage isolation. Addition of mucin to soft-agar culture medium is proposed as an optimized technique for viral titration. This invention also covers all relevant steps in setting up a phage therapy product: phage production, phage quantification and phage isolation.

11 Claims, 6 Drawing Sheets

METHODS AND CULTURE MEDIA FOR PRODUCTION, QUANTIFICATION AND ISOLATION OF BACTERIOPHAGES

FIELD OF THE INVENTION

The present invention relates to the fields of practical bacteriology and applied virology. Particularly, the present disclosure is directed to a method for producing stocks of bacteriophages capable of infecting bacterial species modified by exposure to mucins. The present invention is also based on a modified culture medium for growing bacterial hosts rendering the host cells permissive to phage infection.

BACKGROUND OF THE INVENTION

The majority of antibiotics used today is from intensive farming systems connected to human food production. With the increasing number of antibiotic resistance at hand and the growing concern of associated healthcare problems, the use of antibiotics in food production is at stake due to high amount of environmental leakage. Therefore, the use of bacteriophages (phages) as a selective therapy method to destroy pathogenic bacteria is increasing. These viruses are ubiquitous in the environment, infect only bacteria and are harmless to humans and other animals.

It is known that most infections start from mucosal surfaces, with over 200 known microorganisms capable of invading mucosal layers. Thus, mucosal infections results in mortality and morbidity with clinical and economical importance worldwide (Bradbury 2000, Holmgren & Czerkinsky 2005). Phage-mucus interaction has been proposed as a non-host derived form of mucosal immunity conserved in metazoans (Barr et al. 2013). Phage adhesion to animal mucins may be relevant for phage therapy, including cases in which phage exposure is made in order to enrich the mucus microbiome resulting in preventive and prolonged protection against bacterial pathogens.

*F. columnare* is the etiological agent of *columnaris* disease, a significant problem for fresh water aquaculture around the world. It affects the external mucosal surface of fishes, and is usually treated with antibiotics (mainly oxytetracycline). *Aeromonas* species are also important pathogens of fish, besides causing a large array of known and emerging diseases in humans and other animals (Janda and Abbott 2010). Alternative treatments for fish diseases are welcomed since antibiotic use can be expensive and lead to bacterial resistance. Furthermore, antibiotics do not eradicate the pathogen from the rearing environment, because as an opportunist, it can survive outside the fish host for long periods (several months). One of the alternatives for antibiotics in disease outbreaks is the use of *F. columnare* infecting phages. These organisms are specific and efficient in killing their bacterial hosts, but so far treatment efficacy has only been tested in laboratory settings. Besides, it has been difficult to isolate these viruses from the environment, and to grow them using conventional phage production techniques.

The mucosal surfaces of fish are the environments where *Flavobacterium* and at least some of the infecting phages may naturally interact. The prior art describes survival of *F. columnare* in primary fish mucus and in formulated water containing purified porcine mucin (Staroscik and Nelson 2007; Shoemaker and LaFrentz 2015). Other authors have shown that *F. columnare* has a chemotactic response to primary catfish mucus and that mucus exposure improved extracellular protease activity and upregulated gliding motility gene gdH (Klesius et al. 2008; 2010; Shoemaker and LaFrentz 2015).

One characteristic of the *F. columnare* infecting phages is that it is not possible to produce large quantities of them by using the conventional phage production methods based on liquid cultures. Although other methods can be used, they make the process too time consuming and hard to implement in large scale. Another common issue with *Flavobacterium* phages concerns quantification by titration, since very often the bacterial growth in titration plates is not optimal and the phage enumeration fails, resulting in loss of time and resources. Obtaining new phages from field samples is also crucial for research and for using these organisms in phage therapy, so improved methods for phage isolation can be beneficial. All the three points above are problems that need solving before *columnaris* phage therapy becomes reality.

The interaction of phages with animal mucus has been proposed to be important as a defense against bacterial infections, and has potential to be explored for traditional and preventive phage therapy. The methods presented here were developed using *Flavobacterium columnare* as model, and then shown to be also valid for *Aeromonas* sp, an unrelated bacterium, revealing that the methods can be applied to other groups of bacteria and phages.

SUMMARY OF THE INVENTION

By studying how *F. columnare* and its phages interacts in simulated mucosal cultures composed of growth media supplemented with primary fish mucus or purified porcine mucin, we discovered that mucin/mucus exposure modifies the bacterial physiology making it more virulent and at the same time susceptible for phage infections. The increased susceptibility derived from mucin exposure was then used to create the methods related to phage production, quantification and isolation. We verified that the effect on FCL-2 phage growth is similar when using primary fish mucus and purified porcine mucin, showing that mucins, be it purified or a mixture found in animal mucosa, are equally effective and the key ingredient for the invention. The use of purified porcine mucin is preferred over primary mucus because of purity and reproducibility issues.

Since the close relationship with mucus is not exclusive to *F. columnare*, as many other bacteria thrives in metazoan mucus layers and uses it as a gateway to cause disease, it was expected that the methods would also apply to other species in which mucin acts as a modifier of bacterial genetic and phenotypic states. This has been tested and proved by showing that *Aeromonas* sp strain B135 and phage V46 behave similarly to *F. columnare* and phage FCL-2 in mucin cultures. Phage V46 does not grow well in liquid cultures, but addition of purified porcine mucin or primary fish mucus results in B135 biofilm formation and efficient V46 growth and isolation from media containing small amounts of phages. A third phage-bacteria pair composed of *Aeromonas* sp strain B158 and phage V61 was also tested and shown to behave similarly in phage isolation conditions using mucin.

The culture medium and methods we propose as invention here (1) improve the production of phages capable of infecting bacterial species that responds to mucins by hundreds to thousands fold when compared to the conventional method of phage production; (2) improve the titration of phages on soft agar cultures making the method reproducible by helping in the formation of bacterial lawns; and (3) makes phage isolation from field samples or solutions containing small quantities of phages easier and more efficient by exploiting the phage susceptible state generated by exposing bacteria to mucin. The present inventors have thus surprisingly discovered that a modified culture media supplemented with mucin provides all these improvements.

The present invention is thereby directed to a use of a culture medium comprising essential nutritional ingredients for the growth of bacteria and mucin or another mucus component as a supplement for inducing changes in the bacterium cells that facilitates phage growth.

The present invention is also directed to a method for producing bacteriophages infecting bacterial hosts modified by mucin exposure comprising the steps of:
  a) adding bacterial cells to a sterile culture medium supplemented with mucin or another mucus component,
  b) incubating said culture medium, thereby obtaining a bacterial culture modified by mucin exposure,
  c) optionally collecting the supernatant containing floating (planktonic) bacterial cells from said culture and transferring the cells to a new container in order to discard most of the biofilm,
  d) adding a bacteriophage infecting the bacterial host to the bacterial culture obtained from step b) or c),
  e) incubating the culture obtained in step d) until the culture is ready for phage collection.

Another aspect of the present invention is to provide a method for determining the number of plaque-forming phage particles in a bacteriophage stock or a sample comprising or suspected to comprise bacteriophages infecting a bacterial host to be tested, the method comprising the steps of:
  a) preparing a sterile semi-solid culture medium supplemented with mucin or another mucus component,
  b) adding aliquots of the bacterial host grown in a culture medium and a dilution of the bacteriophage stock or sample to an aliquot of the semi-solid culture medium obtained in step a) and plating the mix on an agar plate or a Petri dish; or alternatively adding an aliquot of bacterium grown in a culture medium to an aliquot of the semi-solid culture medium obtained in step a) and plating the mix on an agar plate or a Petri dish and adding a dilution of the bacteriophage stock or sample on top of the plated mix;
  c) repeating the previous step with a different dilution of said bacteriophage stock or sample, wherein each mix is plated on a separate agar plate or Petri dish;
  d) incubating the plates obtained in steps b) and c); and
  e) determining the number of bacteriophage particles in the stock or sample by counting plaques on the plates.

Another aspect of the invention is a semi-solid culture medium for growing bacterial cells comprising essential nutritional ingredients for the growth of bacteria and mucin or another mucus component as a supplement.

FIG. 3: Comparison of the mucin effect for phage growth between V46 (*Aeromonas* sp phage) and FCL-2 (*F. columnare* phage). A) Phage V46 growth curve in *Aeromonas* sp strain B135 control cultures, control cultures supplemented with mucin at the time of infection or cultures exposed to mucin 22 h before infection. B) Phage FCL-2 growth curve in *F. columnare* strain B185 control cultures, control cultures supplemented with mucin at the time of infection or cultures exposed to mucin 22 h before infection.

FIG. 4. Optimized phage titration method and examples of bacterial lawns formed using soft-agar Shieh or soft-agar-mucin Shieh. A) Recommended general protocol for optimized *F. columnare* infecting phages titration. B) *F. columnare* strain B245 lawns formed on soft-agar Shieh (left) and on soft-agar-mucin Shieh (right). C) *F. columnare* strain B067 lawns formed on soft-agar Shieh (left) and on soft-agar-mucin Shieh (right). D) *F. columnare* strain B185 lawns formed on soft-agar Shieh (left) and on soft-agar-mucin Shieh (right).

FIG. 5. Optimized phage isolation method. A) Overview of the proposed isolation protocol based on *F. columnare* mucin cultures. B) Example of a titration plate used for screening six different enrichment cultures.

FIG. 6: Comparison of the mucin effect for phage isolation between two *Aeromonas* sp strains and *F. columnare*. A) Recovery of phage V46 using *Aeromonas* sp B135 using control cultures, mucin cultures or both either supplemented with LB media or LB media and mucin at the time of preparation of the enrichment cultures. B) Recovery of phage V61 using *Aeromonas* sp B158 using control cultures, mucin cultures or both either supplemented with LB media or LB media and mucin at the time of preparation of the enrichment cultures. C) Recovery of phage FCL-2 using *F. columnare* B185 using control cultures, mucin cultures or both either supplemented with LB media or LB media and mucin at the time of preparation of the enrichment cultures.

DETAILED DESCRIPTION OF THE INVENTION

The abbreviation "cfu" used below is known in the art and refers to colony-forming unit used to estimate the number of viable microbes in a sample or aliquot. The abbreviation

"pfu" refers in the art to a plaque-forming unit, i.e. a measure of the number of phage particles causing lysis of the infected host cell and thus forming a plaque of dead cells within a confluent lawn of host cells. The abbreviation "moi" is also used in the art and refers to multiplicity of infection, i.e. the ratio of the number of bacteriophage or virus particles to the number of infection targets (i.e. host cells).

The term "planktonic cells" refers herein to single-cells that may float or swim in a liquid medium. Planktonic cells are usually physiologically distinct from the cells of the same organism growing in a biofilm.

Bacteriophages are a group of viruses that infect bacteria, and are thus distinct from the animal and plant viruses. Bacteriophages replicating through a lytic cycle cause lysis of the host bacterial cell as a normal part of their life cycles. The natural capability of these phages to infect and kill bacteria, together with the specificity of the phage-bacterial interactions, is the basic phenomena on which the concept of phage therapy is built. Therefore, phages that possess lytic life cycle are suitable candidates for phage therapy.

Those skilled in the art are capable of growing bacteriophage in the bacterial host using conventional methods. Bacteriophage stocks can be generated by growing the phage in a liquid medium containing the target organism, i.e. the bacterial host. Growth of bacteriophage on plates comprising a layer of a solid phase (bottom layer) and a layer of semi-solid phase (top layer) is another known procedure to one skilled in the art, wherein the phage-bacteria mixture is added to the semi-solid culture medium and the semi-solid medium is spread on a solid phase in a plate (e.g. a Petri dish). The commonly used procedure for obtaining such plates is to use an agar concentration of 0.8-1.5% to obtain the solid layer and an agar concentration of 0.7% in the semi-solid medium. Other gel-forming reagents than agar can also be used for solid and semi-solid medium. The plate method is specifically used for phage titration (i.e. the determination of the number of active phage particles in a stock) and also when localization and isolation of a specific, single bacteriophage strain from the plate is desired.

The aim of the present invention is to improve the production of phages capable of infecting bacterial species modified by exposure to mucins, such as *Flavobacterium columnare* or *Aeromonas* sp, by providing a modified culture medium for growing the bacterial hosts, the medium comprising essential nutritional ingredients for the growth of bacteria and mucin or another mucus component, preferably purified mucin, more preferably purified porcine mucin, such as porcine type III mucin, as a supplement. The concentration of mucin in the medium is preferably 0.0001-1% (w/v), more preferably 0.001-1% (w/v), most preferably 0.01-0.2% (w/v).

Mucin is the main component of mucus and its presence changes several aspects concerning how the bacteria grow and its characteristics. The changes that occur in the mucin containing growth media also makes the bacteria more prone to viral infections and results in the increased viral yield and improved viral recovery obtained. The changes elicited by mucin exposure can be defined as biofilm formation, motility changes, modifications in the cell surface molecules and/or regulation of gene expression.

Mucin presence is not an issue to the final phage product since it is easily removed from the system by the common virus purification procedures. The costs of producing viruses using this method are not significantly higher since the only extra ingredient needed is the mucin.

In alternative embodiments of the invention, the culture medium of the invention can be liquid medium, solid medium, or a semi-solid medium such as a soft-agar. For scaling-up, the liquid medium is preferred. Culture media comprising essential nutritional ingredients for the growth of bacteria are well-known in the art. In an embodiment, the culture medium of the present invention comprises at least peptone and/or yeast extract to support the growth of bacteria, preferably the medium comprises the ingredients of Shieh recipe or, e.g., Reasoner's 2A agar (R2A agar) or lysogeny broth (LB). The selection of the suitable medium depends on the targeted bacterial species.

The peptone used in the culture medium can be any water-soluble mixture of polypeptides and amino acids formed by the partial hydrolysis of a protein source. Yeast extracts comprise various forms of processed yeast products made by extracting the cell contents of the yeast cells (i.e. removing the cell walls of the yeast cells). An example of the ingredients of preferred Shieh broth/agar is as follows (adapted from Song et al., 1988): peptone (e.g. by Difco™, Detroit, Mich.), 5 g/liter; yeast extract (e.g. by Difco™), 0.5 g/liter; sodium acetate($H_2O$)$_3$, 0.0166 g/liter; $BaC_2(H_2O)_2$, 0.01 g/liter; $K_2HPO_4(H_2O)_3$, 0.132 g/liter; $KH_2PO_4$, 0.05 g/liter; $MgSO_4 7H_2$, 0.3 g/liter; $CaC_2(H_2O)_2$, 0.0067 g/liter; $FeSO_4 7H_2O$, 0.001 g/liter; $NaHCO_3$, 0.05 g/liter; distilled water (pH 7.2), 1,000 ml, in case of agar medium, add agar 10 g/liter.

In a preferred embodiment of the present invention, said medium is a rich medium supporting exponential growth of the bacteria. Other nutrient medium which support bacterial growth, and even mucin added to autoclaved water, can also be used since mucin is the key ingredient. In case of using pure water with mucin the bacterial growth and phage yields are not optimal, so dilution of mucin in a culture medium is recommended.

In another embodiment, the present invention is also directed to a use of a culture medium comprising essential nutritional ingredients for the growth of a bacterium and mucin or another mucus component as a supplement for producing a stock of bacteriophages infecting said bacterium. In a preferred embodiment, the present invention is directed to a use of the culture medium as defined above for culturing bacteria of the genus *Flavobacterium* and *Aeromonas*. Preferably, said *Flavobacterium* is *Flavobacterium columnare*. The present invention thus enables production of bacteriophage stocks infecting *Flavobacterium columnare*.

In another important embodiment, the present invention is directed to a method for producing bacteriophages infecting bacterial hosts modified by mucin exposure comprising the steps of:

a) adding bacterial cells to a sterile culture medium supplemented with mucin or another mucus component, the bacterial cells preferably representing a strain of *Flavobacterium* or *Aeromonas* sp,
b) incubating said culture medium, thereby obtaining a bacterial culture modified by mucin exposure,
c) optionally collecting the supernatant containing floating (planktonic) bacterial cells from said culture and transferring the cells to a new container in order to discard most of the biofilm,
d) adding a bacteriophage infecting the bacterial host to the bacterial culture obtained from step b) or c),
e) incubating the culture obtained in step d) until the culture is ready for phage collection, i.e. the phage yield increases or peaks.

In order to produce a stock of bacteriophages infecting the bacterial host, the method preferably comprises a further step of:

f) preparing a bacteriophage stock from the culture obtained in step e).

In order to perform phage titration, the method preferably comprises further steps of:

g) preparing a sterile semi-solid culture medium supplemented with mucin or another mucus component, preferably purified mucin, and h) adding aliquots of the bacterium grown in a culture medium, preferably supplemented with mucin or another mucus component, and a dilution of the bacteriophage stock obtained in step f) to an aliquot of the semi-solid culture medium obtained in step g) and plating the mix on an agar plate or a Petri dish; or alternatively adding an aliquot of the bacterium grown in a culture medium, preferably supplemented with mucin or another mucus component, to an aliquot of the semi-solid culture medium obtained in step g) and plating the mix on an agar plate or a Petri dish and adding a dilution of the bacteriophage stock obtained in step f) on top of the plated mix; i) repeating the previous step with a different dilution of said bacteriophage stock, wherein each sample is plated on a separate agar plate or Petri dish;

j) incubating the plates obtained in steps h) and i); and k) determining the number of bacteriophage particles in the stock by counting plaques on the plates.

In a specific embodiment, the method is directed to isolation of new bacteriophage strains from environmental samples, wherein the bacteriophage infecting *Flavobacterium columnare* added to said bacterial culture in step d) is provided by an environmental sample such as a water sample, a fish tank water sample or a fish mucus or tissue sample or by any kind of a sample known or suspected to contain *Flavobacterium* infecting phages such as biofilms and sediments. Enrichment cultures and phage stocks of steps e) and f) are then sampled and phage presence determined by the phage titration method described by steps g) to k). Obtained plaques can be collected and further purified or grown by the methods described above.

In a separate embodiment, the present disclosure is directed to a method for determining the number of plaque-forming phage particles in a bacteriophage stock or a sample comprising or suspected to comprise bacteriophages infecting a bacterial host, the method comprising the steps of:

a) preparing a sterile semi-solid culture medium supplemented with mucin or another mucus component, b) adding aliquots of bacterium grown in a culture medium and a dilution of the bacteriophage stock or sample to an aliquot of the semi-solid culture medium obtained in step a) and plating the mix on an agar plate or a Petri dish; or alternatively adding an aliquot of bacterium grown in a culture medium to an aliquot of the semi-solid culture medium obtained in step a) and plating the mix on an agar plate or a Petri dish and adding a dilution of the bacteriophage stock or sample on top of the plated mix;

c) repeating the previous step with a different dilution of said bacteriophage stock or sample, wherein each mix is plated on a separate agar plate or Petri dish;

d) incubating the plates obtained in steps b) and c); and e) determining the number of bacteriophage particles in the stock or sample by counting plaques on the plates.

Examples of these methods are presented in the Experimental Section below. In conclusion these methods are efficient, not expensive, can be made in larger scales and solve the problem of producing phages against bacterial species such as *F. columnare* and *Aeromonas* sp, at levels high enough required for phage therapy agents or phage research. The method also makes phage quantification more reliable and allows for efficient phage recovery from field samples, making it easier to obtain new phages from nature. Taking all three processes together, we propose a full optimized package with applicability for phage therapy products development, covering from phage isolation to phage production and phage quantification. Each of these three steps has been made more efficient and reliable by our methods.

Accordingly, the present invention also provides a kit for growing bacterial species and phages infecting the bacteria, the kit comprising one or more containers comprising reagents for preparing a culture medium suitable for growing the bacteria and a container comprising mucin or another mucus component, preferably purified mucin such as purified porcine mucin. Preferably said reagents are selected from the group consisting of: peptone, yeast extract, minerals and vitamins. More preferably, said culture medium is Shieh medium or LB medium.

Figure 1:
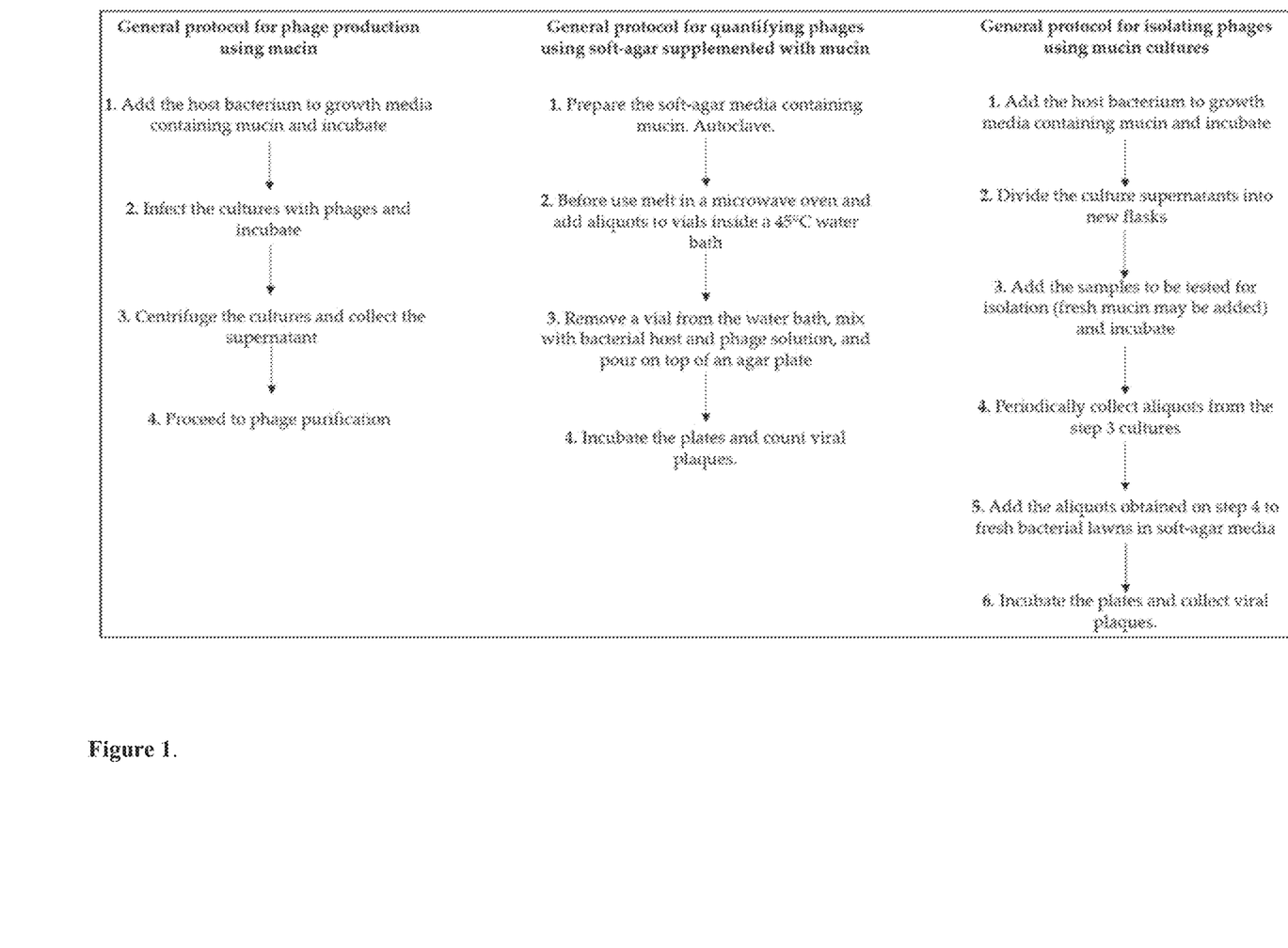
FIG. 1. Preferred protocol guidelines for phage production, quantification and isolation using mucin cultures. Specific details, such as incubation times, concentrations and temperatures, are dependent on the bacterial host and phages used and are easily optimized by a person skilled in the art.

Preferred protocols for the present methods are the following (these are also outlined in FIG. 1):

1) Preferred Protocol for Phage Production Using Mucin 1.1. Add the desired bacterial host to liquid cultures containing 0.1% mucin in its composition. Incubate at the adequate temperature and rotation speed.

Mucin concentration can vary from 2 to 0.001%.

Temperature is determined by the optimal growth of the bacteria.

Rotation should allow the biofilm to form at the liquid-air interface of the flasks.

1.2. After mucin exposure infect the bacteria with phages and incubate the cultures.

Mucin exposure time varies depending on how long the bacteria needs to be modified by mucin. If a high amount of cells is added in step 1.1, no incubation is needed (in this case add the cells to the mucin culture and infect right away).

For some phages it is important to expose the hosts to mucin for several hours, then collect the liquid (plankton) and discard the biofilm. For these cases only the plankton is infected after the step 1.1 incubation.

The amount of phages used for infection can vary, preferably aim for a moi of 0.01.

1.3. Centrifuge the cultures after infection to remove bacterial cells, cell debris and mucin.

Collection time can vary from 4 to 72 hours, depending on the phage.

1.4. Collect the supernatant and proceed to virus purification or quantification following standard protocols.

2) Preferred Protocol for Quantifying Phages With Bacterial Lawns Using Soft-Agar-Mucin Growth Media 2.1. Prepare the medium by adding 0.1% (w/v) mucin to the normal soft-agar recipe.

Mucin concentration can vary from 1 to 0.001%.

2.2. Autoclave (121 degrees, 15 minutes) immediately and store at room temperature.

2.3. Before using melt the media in a microwave oven and pipet 3 ml to a glass vial inside a 45 degrees water bath.

2.4. Remove the vial from the water bath, wait for cool down and then add 200-300 µl of bacteria from a previously prepared fresh overnight culture. Pour on top of an agar plate.

The viruses to be titrated can either be mixed in the 200-300 µl volume containing the bacteria or dropped on top of the soft-agar-mucin media layer immediately after the preparation of the plates.

2.5. Incubate the plates for 2 to 3 days at room temperature for the growth of the bacterial lawns.

3) Preferred Protocol for Isolating Phages Using Mucin Cultures 3.1. Prepare bacteria cultures in growth media and incubate at the adequate temperature and rotation speed.

If needed the media in this stage can contain 0.1% mucin (but can vary from 2 to 0.001%).

3.2. On the next day divide the cultures supernatant into new tubes (if using a 5 ml culture in step 3.1, divide it into five aliquots of 1 ml in this step).

3.3. Add the solutions to be tested for phage isolation to the tubes prepared in step 3.2. As an example 4 ml of solution can be added to the 1 ml cultures made in step 3.2.

If mucin was not added in step 3.1, add it to the cultures made in this step. If it was present in step 3.1, it can be omitted or renewed on this step. An optimal final concentration is 0.1%, (but can vary from 2 to 0.001%).

3.4. Sample periodically the enrichment cultures made in step 3.3 and test for phage presence by titration.

3.5. If plaques appear, collect them and proceed to viral growth and purification.

The following examples are given to further illustrate embodiments of the present invention, but are not intended to limit the scope of the invention. It will be obvious to a person skilled in the art, as technology advances, that the inventive concept can be implemented in various ways. The invention and its embodiments are thus not limited to the examples described herein, but may vary within the scope of the claims.

EXPERIMENTAL SECTION

Example 1. *Flavobacterium columnare* Phage Production Using Mucin

Figure 2:
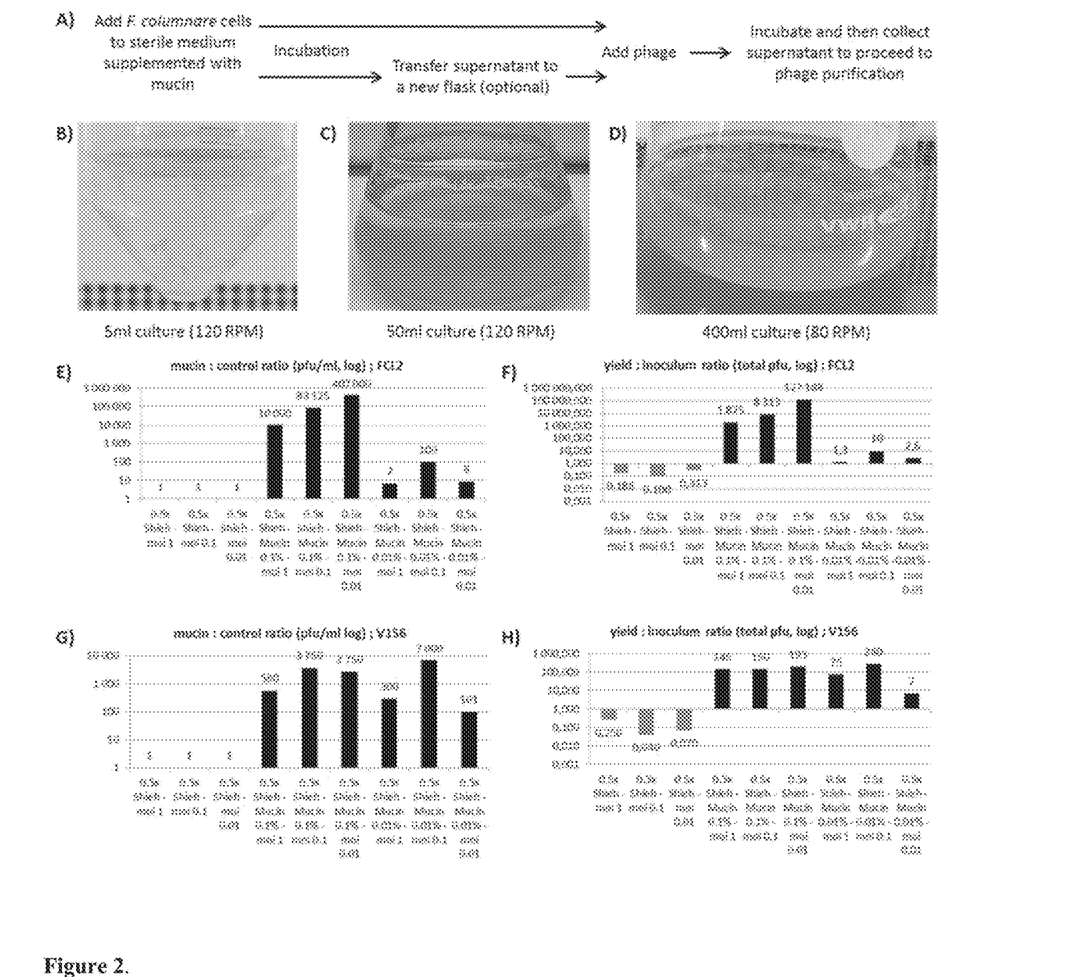
FIG. 2. Optimized phage production method. A) Recommended general protocol for optimized *F. columnare* infecting phages production. B) Example of a 5 ml culture of *F. columnare* made in culture medium supplemented with mucin. Picture taken after 22 hours of incubation (right before collecting the supernatant for making the infection). Note the long, stringy, biofilm. C) Example of a 50 ml culture of *F. columnare* made in culture medium supplemented with mucin. Picture taken at the time of collecting the virus containing supernatant (22 h of growth, plankton collected and infected for 24 h). Note that the biofilm reappears during the infection. D) Example of a 400 ml *F. columnare* made in culture medium supplemented with mucin. Picture taken at the time of collecting the virus containing supernatant (22 h of growth followed by 24 h of infection, no separation between biofilm and plankton prior to infection). Note that a lower rotation was used to minimize biofilm detachment when using this larger volume. E) Example of phage FCL-2 production on *F. columnare* B185 strain, shown as the ratio between virus yield in mucin cultures divided by the yield in control cultures. F) Same as in E, but shown as the ratio between total virus yield divided by the inoculum. G) Example of phage V156 production on *F. columnare* B245 strain, shown as the ratio between virus yield in mucin cultures divided by the yield in control cultures. H) Same as in G, but shown as the ratio between total virus yield divided by the inoculum. Note that the optimal moi and mucin concentration varies according to the virus-host pair, and that virus yield is negative in control cultures.

1. $5 \times 10^4$ cfu of *F. columnare* strain B185 or B245, from a fresh overnight culture, were added to five millilitres of 0.5× Shieh supplemented with 0.1% porcine mucin. Control cultures were also prepared by adding the same amount of cells to the same volume of 0.5× Shieh cultures without the supplementation. The samples were incubated at 25 degrees under 120 rpm (80 rpm if larger volumes were used in glass flasks). The formation of a thick biofilm ring on the liquid-air interface and clear or slightly turbid liquid is a good indication of appropriate culturing conditions. Examples are shown in FIG. 2.

Mucin concentration can vary, e.g., from 1 to 0.01%. For scaling up, $10^4$ cfu/ml can be used as inoculum. If cell number quantification is not possible, the fixed volume of 15 µl of a 1/100 dilution of an overnight *F. columnare* turbid culture can be used per 5 ml of culture, with some impact to the optimal phage yield at the end.

2. After 22 hours, a spectrophotometer was set to 595 nm and $OD_{595}$ of the control cultures was measured to calculate the amount of viruses to be used for infection (the OD was measured from the controls because it is more homogeneous. The mucin culture at this point had biofilm formed and clearer supernatant, so OD measurements would not have been reliable to estimate the real number of cells). Optical density to cfu conversion is calculated by a previously established standard curve.

The incubation time can vary between 18 to 24 hours.

3. All the supernatant from the mucin cultures was removed and transferred to a new flask or vial by pouring. This supernatant contained the planktonic cells which will be infected.

3.1. Alternatively, the original mucin culture can be used directly for viral growth in case of biofilm infecting phages.

4. Following the step 3 or 3.1, the bacteria were infected with bacteriophage strain FCL-2 (B185 as host) or V156 (B245 as host) using a moi of 0.01. Moi can vary from 1 to 0.001. If cell number quantification is not possible for moi calculation, $3 \times 10^6$ viruses can be added as inoculum for each 5 ml of culture, with some impact to the optimal phage yield at the end.

5. The cultures were centrifuged (Sorvall SLA rotor, 8000 rpm, at 4 degrees Celsius, 15 minutes) 24 hours after infection to remove bacterial cells, cell debris and mucin.

Collection time can vary from 4 to 48 hours.

6. The supernatant was collected and then followed virus purification or quantification by standard protocols.

The conditions above have been tested for FCL2-B185 and V156-B245 pairs, and may vary slightly if other bacteria or phage are used. In the case of a new or untested phage, using the proposed approach can be a good starting point but improvements can be made by changing conditions especially in steps 1 and 4, and also by comparing step 3 to 3.1 infections.

Results and Discussion

Different approaches were used to study *F. columnare* and phage interactions in mucin. For all tests the FCL2-B185 phage-bacteria pair was used as models. *F. columnare* strain B185 was chosen because it has been shown to be virulent and thus relevant as a *columnaris* disease causing agent, while phage FCL-2 has been shown before to be efficient as phage therapy tool (Laanto et al. 2011; 2015). As negative controls, we used bacterial hosts unrelated to *F. columnare* and its phages (*Escherichia coli, Salmonella* and *Flavobacterium* sp), in which no improvement of phage production was detected. Then the *F. columnare* results were validated using V156-B245 phage-host pair and other phages isolated in this study.

Experiments were made by adding phage and bacteria at the same time to mucin cultures, letting the bacteria grow first in mucin before adding the phages, testing different concentrations of Shieh media and mucin, evaluating the best time to harvest the phages, testing different amounts of viral inoculums, and infecting the full mucin cultures or separating its components (biofilm and planktonic cells) before infection.

In the optimal conditions we were able to improve FCL-2 yield by 400.000 times and V156 yield by 7.000 times when compared to controls. It is a significant gain, especially when considering that these viruses do not grow in control liquid cultures. Actually, there is a loss in the total amount of viruses in the control cultures regardless of the inoculum used, which is only avoided if the virus growth is made on mucin cultures. So the mucin cultures not only make the production more efficient but allow it to be made by using liquid cultures, which would be impossible otherwise. The proposed methodology, examples of culture aspect and representative results are shown in FIG. 2.

When three new isolated *F. columnare* bacteriophages were tested in this general protocol, without any type of optimization, the yield improved in mucin cultures over 15.000 times for each. For fourteen other new isolates it was possible to perform virus growth in mucin cultures but no viruses were obtained from control cultures. Our data thus clearly shows that mucin presence in *F. columnare* cultures improves phage infections and progeny production, yielding 1000s to 100000s more viruses than in the control cultures. The process is easy to perform, reproducible, has the potential to be scaled up and is only slightly more expensive than the conventional process. Since the method is based on liquid cultures, it is convenient for large scale commercial production. All tested *F. columnare* strains grew similarly on mucin cultures, making this method applicable to potentially any phage that infects these bacteria.

Example 2: *Aeromonas* sp Phage Growth Using Mucin

While testing different bacterial species from our collection we discovered that *Aeromonas* sp strain B135 also formed biofilm when exposed to mucin. This was taken as a cue that this bacterium could also be targeted by our methods, and we tested this hypothesis by exposing the bacterium to purified mucin or primary fish mucus and testing how its phage, V46, grew. The results revealed a similar pattern to *F. columnare* and phage FCL-2, showing that the methods can also be applied to other species that responds to mucin presence in the cultures, expanding their applicability.

The main difference between *Aeromonas* sp and *F. columnare* is related to the timing of mucin exposure. Probably due to a faster growth rate, exposure to mucin for optimal *Aeromonas* sp phage should be shorter than *F. columnare*. This has been tested and the details are shown below as example of *Aeromonas* sp phage V46 in purified mucin cultures.

1. Five µl of OD 0.02 *Aeromonas* sp strain B135 culture was added to 0.2×LB medium (control, 6 cultures) or 0.2×LB medium supplemented with 0.1% purified porcine mucin (3 cultures).
2. 22 hours later three control cultures received mucin to a final concentration of 0.1% while the remaining three did not receive any mucin. Then, all control and mucin cultures were infected with $2.5 \times 10^5$ pfu of phage V46.
3. At 4, 24 and 48 h after infection samples were taken from the cultures and phages numbers quantified by titration.

As comparison, the same procedure was made using *F. columnare* strain B185 and phage FCL-2. $5 \times 10^4$ cells were used as initial inoculum and $3 \times 10^5$ pfu used for infection.

Results and Discussion

Figure 3:
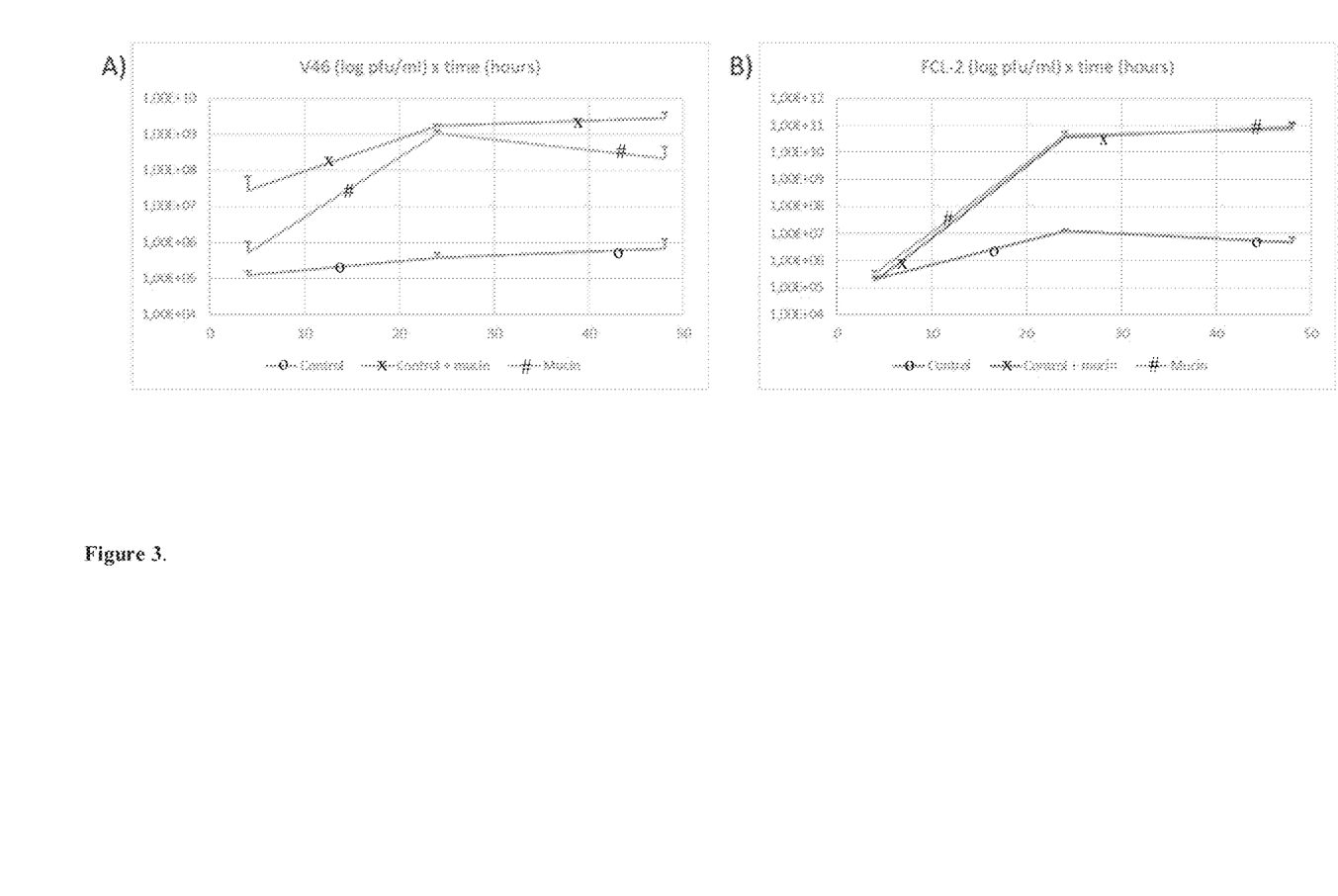

It was possible to detect a positive effect of mucin presence to V46 growth (FIG. 3A). While phage growth was small in control cultures, exposure to mucin (at the time of infection or 22 h previously) greatly improved V46 growth in liquid cultures. V46 growth on 0.2×LB supplemented with 0.1% mucin was 17.000 times higher at 24 h and 60.000 times higher at 48 h after infection. The same trend was verified for FCL-2 in *F. columnare* cells (FIG. 3B), but in this case addition of mucin at the time of infection or 22 hours previously had the same positive effect for FCL-2 production. This proves that mucin exposure of bacterial cells improves phage growth in different bacterial species, not being limited to *F. columnare* only.

Example 3. Method for Producing *Flavobacterium columnare* Lawns Using Soft-Agar-Mucin Shieh for Phage Titrations 1. The culture medium was prepared by adding 0.1% (w/v) porcine mucin to the normal soft-agar Shieh recipe. Mucin concentration can vary from 1 to 0.001%.
2. The medium was autoclaved (121 degrees Celsius, 15 minutes) immediately and stored at room temperature.
3. Before using the media was melted in a microwave oven and 3 ml was pipetted to a glass vial inside a 45 degrees water bath.
4. The vial was removed from the water bath and cooled down, then 200-300 µl of any *F. columnare* strain from previously prepared fresh overnight cultures was added to the vial. A Petri dish containing normal Shieh-agar was then overlayed with the contents of the vial.
5. The plates prepared were incubated for 2 to 3 days at room temperature for the growth of the bacterial lawns.

The viruses to be titrated were either mixed in the 200-300 µl volume containing the bacteria on step 4 or dropped on top of the soft-agar-mucin Shieh layer immediately after the preparation of the plates (10 µl drops per dilution or virus sample).

Results and Discussion

Formation of *F. columnare* uniform bacterial lawn in soft agar cultures is unpredictable and sensitive to variation in culture conditions and batches of the medium used. *F. columnare* tends to aggregate when taken from liquid cultures for use in the process of creating the soft-agar plates for phage titrations. That happens with most strains and prevents the bacterial lawn to form in a homogeneous way, leading to failure in the virus titration. This is frustrating and time consuming since the failure is usually detected only one or two days later, and the titration may have to be started again from the beginning.

Figure 4:
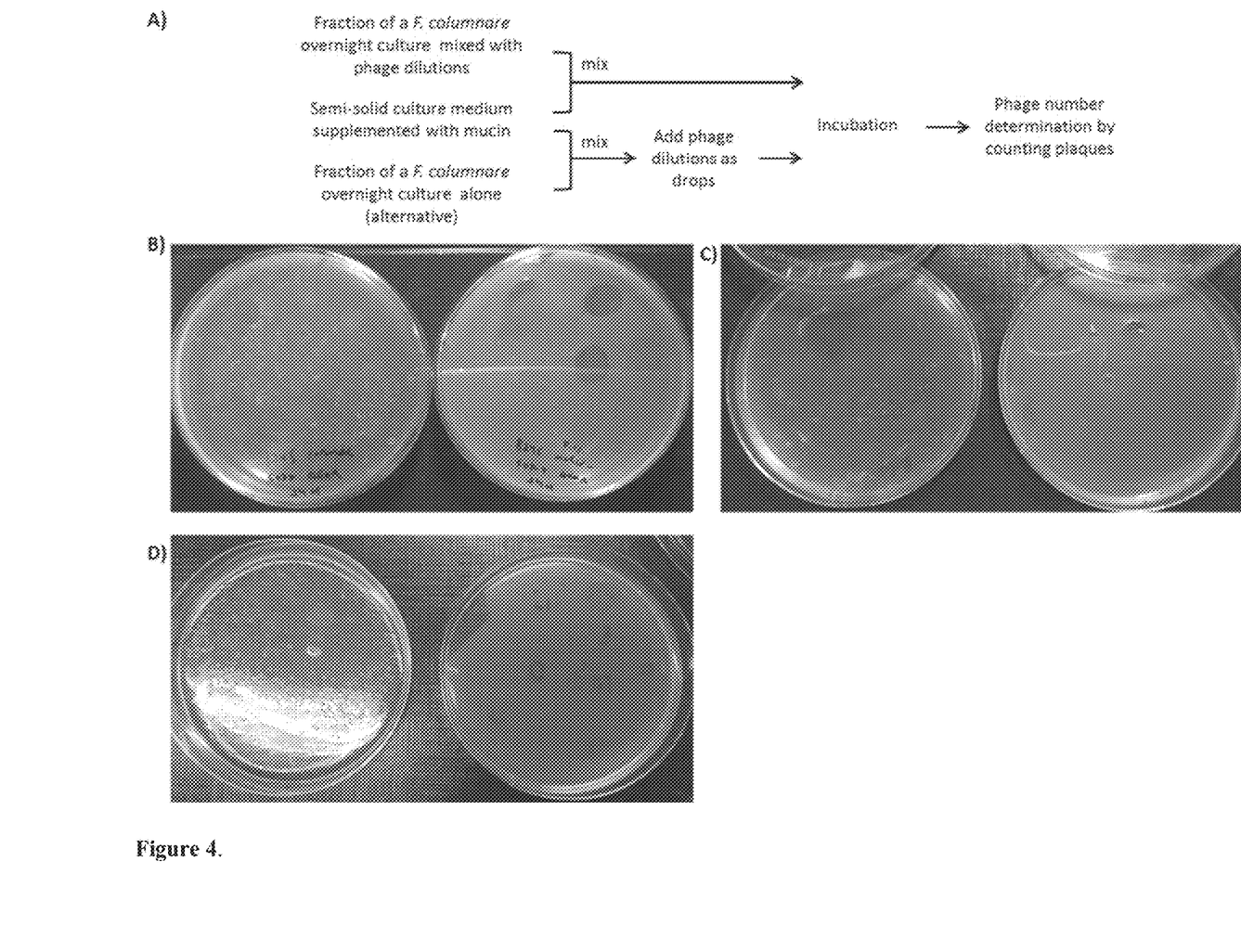

For this process, we have prepared soft agar Shieh media supplemented with 0.1% purified porcine mucin. The mucin was added as powder to the Shieh-agar mix, which was then autoclaved and kept at room temperature. At the time of use the soft-agar-mucin Shieh was melted in a microwave oven and 3 ml were mixed with 200 µl of an overnight grown *F. columnare* culture for preparing the bacterial lawns. While several plates made with soft-agar Shieh ended up with intense clumping and not formed bacterial lawns, the plates made with soft-agar-mucin Shieh had homogeneous lawns formed all the time. Several isolates, from different genotypes, were tested and behaved similarly. The proposed methodology and examples of plates are shown in FIG. 4.

We thus found out that mucin has a positive effect on the improvement of bacterial lawns used for virus titrations. By supplementing soft-agar Shieh with mucin we have solved the problem of variation in the quality of *F. columnare* bacterial lawns used for titrations. It is a very convenient procedure since only requires the addition of an extra ingredient to the formula, and do not need any additional step on the process of making the titration plates. It has been effective with all *F. columnare* strains tested so far, so it has a broad effect and applicability.

Since *Aeromonas* sp and other bacteria in our collection forms confluent bacterial lawns in normal soft-agar, the addition of mucin did not modify nor improved their growth (which is already optimal in the control conditions). However, in the case of other species with difficulty in forming lawns on normal soft agar, mucin could also be useful as in the case of *F. columnare*.

Example 4. Method for Isolating *Flavobacterium columnare* Phages Using Mucin Cultures 1. A *F. columnare* culture was prepared by adding $5.5 \times 10^4$ cfu to 5.5 ml of 0.5× Shieh containing 0.1% porcine mucin and incubated for 22 hours (120 rpm, 25 degrees Celsius).

2. On the next day the culture supernatant (planktonic cells) was divided into five new tubes by adding one ml to each. The tube containing the biofilm was kept (optional).
3. Four ml of the isolation (i.e. environmental) samples were added to each tube (one sample per tube).
3.1. (optional). The biofilm tube can receive a mixture of the samples (1 ml each), if phages that attacks the biofilm are desired. Then it can be processed as the other samples.
4. 200 µl from each culture after 6, 24 and 48 hours was collected and centrifuged (10000 g, 10 minutes, room temperature).
5. 10 µl of each collected sample is added as drops in fresh *F. columnare* bacterial lawns prepared with the protocol described in Example 2.
6. The plates were incubated 2 to 3 days and checked for lysis in the bacterial lawn.

The original cultures can be stored at 6 degrees, the aliquots taken and the collected lysis zones from bacterial lawns can be stored at −20 or −80 degrees, to be used for further characterization of the viruses. The protocol is preferably meant for testing five different samples at the same time, and can easily be adapted for screening more samples or for testing the same five samples in different bacterial hosts at the same time.

Results and Discussion

Initially, viral recovery was tested by adding a small amount of bacteriophage FCL-2 (40 pfu) to autoclaved fish tank water and using that as our isolation samples. Isolations were made in controls (Shieh only) or in Shieh supplemented with mucin, and the effect of full mucin cultures or only biofilms and planktonic cells were tested. No significant improvement in viral recovery was seen in full mucin cultures or in mucin generated biofilms, but when only planktonic cells from mucin cultures were used, viral recovery was over 1,000,000 times higher 24 h after infection when compared to the controls. When pure water was used instead of fish tank water, no viruses were recovered in the controls but around $5\times10^7$ pfu were obtained in the planktonic cells cultures.

The main conclusions are that viruses are only recovered by the conventional isolation process if tank water is present, and that using planktonic cells from mucin cultures makes viral recovery much more efficient and also allows recovery from samples not originated from fish tanks. So the method makes recovery of *F. columnare* phages from conventional field samples easier, and also allows testing of other types of samples.

Figure 5:
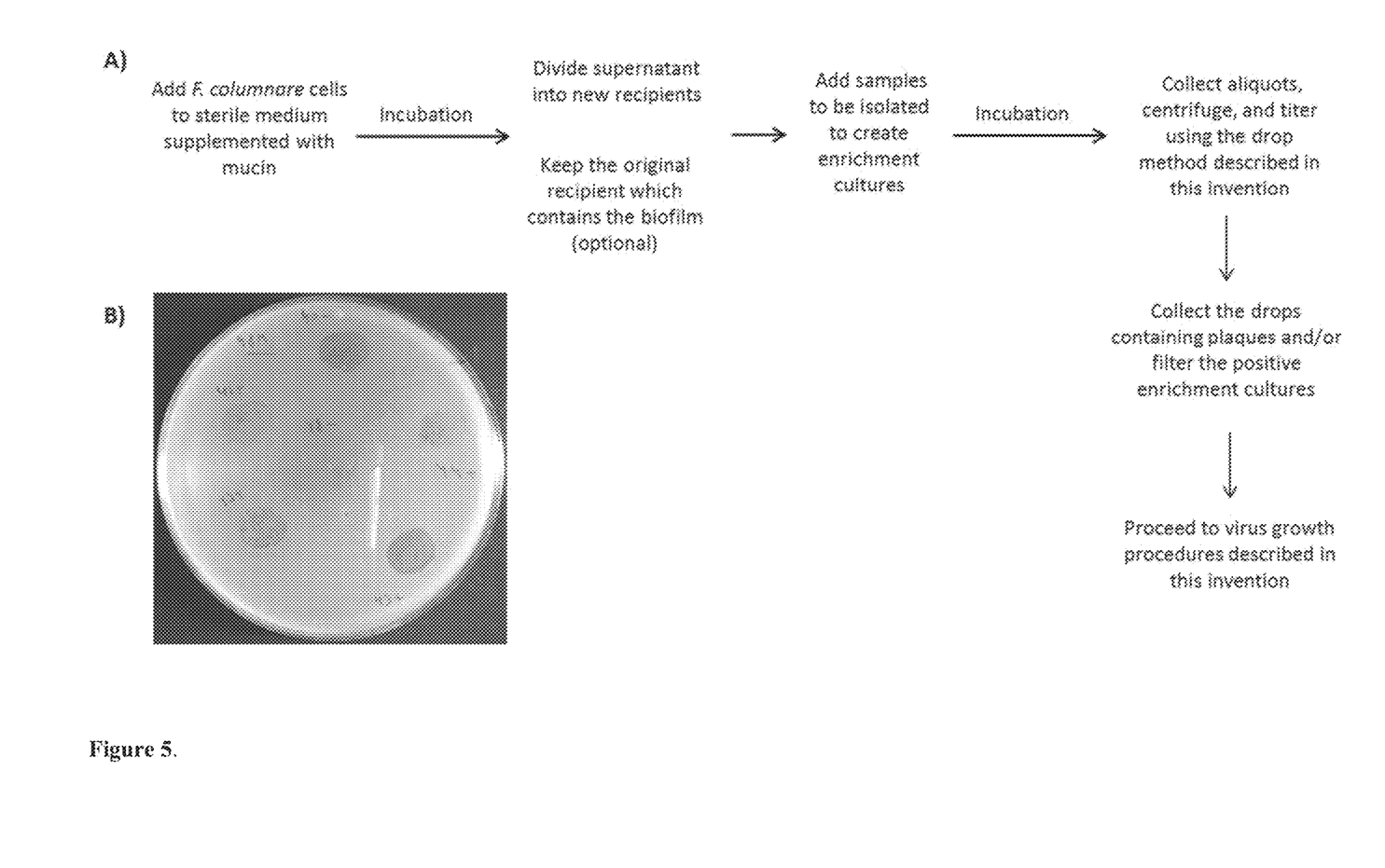

Based on the results above we developed an optimized protocol for isolating *F. columnare* phages from field samples, and tested this protocol in 36 samples obtained from fish farms. An overview of the process is shown in FIG. 5. Virus recovery was satisfactory and, when compared to the standard protocol, less plates and time were needed to achieve the results. As an example: for isolating phages from five samples using four different *F. columnare* strains, the conventional method would have used 60 plates while this method used 12. And since the plates were prepared using the method described in Example 3, no problems with the quality of the bacterial lawns occurred, avoiding the need of repeating the samplings or losing some samples.

Example 5. Method for Isolating *Aeromonas* sp Phages Using Mucin Cultures

Initial tests revealed that for optimal recovery of *Aeromonas* sp phages from solutions containing a small amount of viral particles, mucin exposure must be made at the time of infection and not hours earlier as in the case of *F. columnare*. It may be explained by the faster growth of *Aeromonas* when compared to *F. columnare*. We also verified that a different *Aeromonas* sp strain (B158) can also be modified by mucin exposure to improve recovery of its phage (V61). This shows that another *Aeromonas* sp strain and another phage behaves the same way as *Aeromonas* sp B135-phage V46 and *F. columnare* B185-phage FCL-2. An example of the tests made is shown below.

1. *Aeromonas* sp (strains B135 and B158) were prepared by adding 5 µl of OD 0.02 cultures to 5 ml of 0.2×LB media. Incubation at 25 degrees Celsius and 120 rpm followed.
2. On the next day ml of the cultures were added to 4 ml of: water, water supplemented with LB media (final concentration 0.2×) or water supplemented with LB media and mucin (final concentrations 0.2× and 0.1%, respectively). All cultures contained 50 pfu of phage V46 (for *Aeromonas* sp B135) or V61 (for *Aeromonas* sp B158).
3. At 24 h after infection samples were taken from the cultures and phages numbers quantified by titration.

As comparison, the same procedure was made using *F. columnare* strain B185 and phage FCL-2. $5\times10^4$ cells were used as initial inoculum.

Results and Discussion

Figure 6:
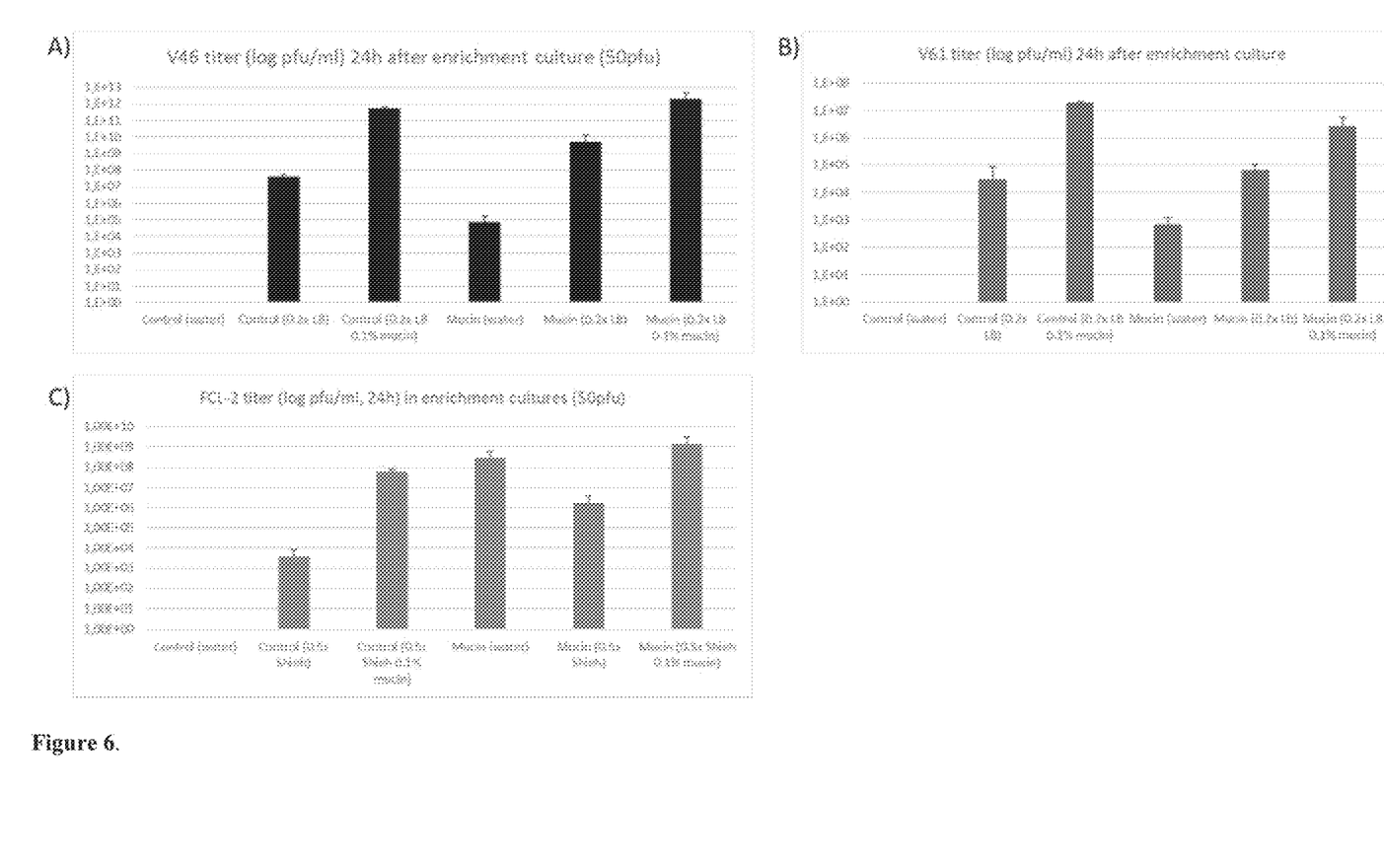

Growing the *Aeromonas* strains in mucin 22 h before adding the cells to phage containing solutions allowed for recovery of phages V46 and V61. The recovery was low, and could be improved by adding mucin straight to the phage containing solutions instead (FIGS. 6A and 6B). Both *Aeromonas* strains tested behaved similarly. The results obtained for *Aeromonas* phages were comparable to the ones shown for *F. columnare* phage FCL-2 (FIG. 6C), with the exception that exposing *F. columnare* cells to mucin 22 h before infection is enough for getting an optimal phage recovery while best phage recovery is achieved for *Aeromonas* by adding mucin to the phage containing solutions.

REFERENCES

Barr, J. J., R. Auro, M. Furlan, K. L. Whiteson, M. L. Erb, J. Pogliano, A. Stotland, et al. 2013. Bacteriophage adhering to mucus provide a non-host-derived immunity. Proceedings of the National Academy of Sciences 110:10771-10776.

Bradbury J. Mucosal infection yields to new approaches. Lancet. 2000; 356(9238):1332. doi:10.1016/S0140-6736(05)74239-2

Holmgren J, Czerkinsky C. Mucosal immunity and vaccines. Nat Med. 2005; 11(4S):S45. doi:10.1038/nm1213

Janda J M, Abbott S L. The genus *Aeromonas*: Taxonomy, pathogenicity, and infection. Clin Microbiol Rev. 2010. doi:10.1128/CMR.00039-09

Klesius, P. H., C. A. Shoemaker, and J. J. Evans. 2008. *Flavobacterium columnare* chemotaxis to channel catfish mucus. FEMS Microbiology Letters 288:216-220.

Klesius, P. H., J. W. Pridgeon, and M. Aksoy. 2010. Chemotactic factors of *Flavobacterium columnare* to skin mucus of healthy channel catfish (Ictalurus punctatus). FEMS Microbiology Letters 310:145-151.

Laanto, E., J. K. H. Bamford, J. J. Ravantti, and L.-R. Sundberg. 2015. The use of phage FCL-2 as an alternative to chemotherapy against *columnaris* disease in aquaculture. Frontiers in microbiology 6.

Laanto, E., L.-R. Sundberg, and J. K. H. Bamford. 2011. Phage specificity of the freshwater fish pathogen *Flavobacterium columnare*. Applied and environmental microbiology 77:7868-7872.

Shoemaker, C. A., and B. R. LaFrentz. 2015. Growth and survival of the fish pathogenic bacterium, *Flavobacterium columnare*, in tilapia mucus and porcine gastric mucin. FEMS Microbiology Letters 362.

Song, Y. L., Fryer, J. L., Rohovec, J. S. 1988. Comparison of Six Media for the Cultivation of Flexibacter *columnaris*. Fish Pathology 23:91-94.

Staroscik, A. M., and D. R. Nelson. 2007. The influence of salmon surface mucus on the growth of *Flavobacterium columnare*. Journal of Fish Diseases 31:59-69.

The invention claimed is:

1. A method for producing bacteriophages comprising the steps of:
   a) adding bacterial cells to a sterile culture medium supplemented with mucin,
   b) incubating said culture medium, thereby obtaining a bacterial culture modified by mucin exposure,
   c) optionally removing a biofilm from said bacterial culture,
   d) adding a bacteriophage capable of infecting the bacterial cells to the bacterial culture obtained from step b) or c), and
   e) incubating the bacterial culture obtained in step d) until the culture is ready for phage collection.

2. The method according to claim 1, further comprising:
   f) preparing a bacteriophage extract from the bacterial culture obtained in step e), thereby producing a stock of bacteriophages.

3. The method according to claim 2, further comprising:
   g) preparing a sterile semi-solid culture medium supplemented with mucin,
   h) adding aliquots of bacterium grown in a culture medium and a dilution of the bacteriophage stock obtained in step f) to an aliquot of the semi-solid culture medium obtained in step g) and plating the mix on an agar plate or a Petri dish; or alternatively adding an aliquot of bacterium grown in a culture medium to an aliquot of the semi-solid culture medium obtained in step g) and plating the mix on an agar plate or a Petri dish and adding a dilution of the bacteriophage stock obtained in step f) on top of the plated mix;
   i) repeating the previous step with a different dilution of said bacteriophage stock, wherein each mix is plated on a separate agar plate or Petri dish;
   j) incubating the plates obtained in steps h) and i); and
   k) determining the number of bacteriophage particles in the stock by counting plaques on the plates.

4. The method according to claim 1, wherein the bacteriophage added to said bacterial culture in step d) is provided by an environmental sample or any sample suspected of containing bacteriophages infecting the tested bacterial host.

5. The method according to claim 1, wherein said bacterial cells represent a strain of *Flavobacterium columnare* or *Aeromonas* sp.

6. A method for determining the number of plaque-forming phage particles in a bacteriophage stock or a sample comprising or suspected to comprise bacteriophages capable of infecting a bacterial host, the method comprising the steps of:
   a) preparing a sterile semi-solid culture medium supplemented with mucin,
   b) adding aliquots of the bacterial host grown in a culture medium and a dilution of a bacteriophage stock or sample to an aliquot of the semi-solid culture medium obtained in step a) and plating the mix on an agar plate or a Petri dish; or alternatively adding an aliquot of bacterium grown in a culture medium to an aliquot of the semi-solid culture medium obtained in step a) and plating the mix on an agar plate or a Petri dish and adding a dilution of the bacteriophage stock or sample on top of the plated mix;
   c) repeating the previous step with a different dilution of said bacteriophage stock or sample, wherein each mix is plated on a separate agar plate or Petri dish;
   d) incubating the plates obtained in steps b) and c); and
   e) determining the number of bacteriophage particles in the stock or sample by counting plaques on the plates.

7. The method according to claim 6, wherein said bacterial host is a strain of *Flavobacterium columnare* or *Aeromonas* sp.

8. A culture medium for producing a stock of bacteriophages comprising essential nutritional ingredients for the growth of a bacterial host and mucin as a supplement, wherein said culture medium is a liquid medium, a solid medium, or a soft-agar medium, and wherein said culture medium is prepared according to Shieh recipe or Reasoner's 2A agar recipe.

9. The culture medium according to claim 8 comprising 0.001-1% (w/v) mucin.

10. The culture medium according to claim 9 comprising 0.01-0.2% (w/v) mucin.

11. The culture medium according to claim 8, wherein said mucin is purified mucin.

\* \* \* \* \*